(12) United States Patent
Will

(10) Patent No.: US 11,944,629 B2
(45) Date of Patent: *Apr. 2, 2024

(54) CONCENTRATED METHOTREXATE SOLUTIONS

(71) Applicant: MEDAC GESELLSCHAFT FUER KLINISCHE SPEZIALPRAEPARARATE MBH, Wedel (DE)

(72) Inventor: Heiner Will, Hamburg (DE)

(73) Assignee: MEDAC GESELLSCHAFT FUER KLINISCHE SPEZIALPRAEPARARATE MBH, Wedel (DE)

( * ) Notice: Subject to any disclaimer, the term of this patent is extended or adjusted under 35 U.S.C. 154(b) by 58 days.

This patent is subject to a terminal disclaimer.

(21) Appl. No.: 16/800,584

(22) Filed: Feb. 25, 2020

(65) Prior Publication Data

US 2020/0246342 A1 Aug. 6, 2020

Related U.S. Application Data

(60) Continuation of application No. 16/152,463, filed on Oct. 5, 2018, now Pat. No. 10,610,531, which is a continuation of application No. 15/592,882, filed on May 11, 2017, now abandoned, which is a continuation of application No. 14/635,542, filed on Mar. 2, 2015, now abandoned, which is a continuation of application No. 14/195,117, filed on Mar. 3, 2014, now abandoned, which is a division of application No. 12/374,528, filed as application No. PCT/EP2007/006491 on Jul. 20, 2007, now Pat. No. 8,664,231.

(30) Foreign Application Priority Data

Jul. 21, 2006 (DE) ............... 10 2006 033 837.5

(51) Int. Cl.
| | |
|---|---|
| *A61K 31/519* | (2006.01) |
| *A61K 9/00* | (2006.01) |
| *A61K 9/08* | (2006.01) |
| *A61K 47/02* | (2006.01) |

(52) U.S. Cl.
CPC .......... *A61K 31/519* (2013.01); *A61K 9/0019* (2013.01); *A61K 9/08* (2013.01); *A61K 47/02* (2013.01)

(58) Field of Classification Search
None
See application file for complete search history.

(56) References Cited

U.S. PATENT DOCUMENTS

| | | | |
|---|---|---|---|
| 4,357,971 A | 11/1982 | Friedman | |
| 5,279,586 A * | 1/1994 | Balkwill | A61M 5/3158 |
| | | | 222/309 |
| 5,542,934 A | 8/1996 | Silver | |
| 5,593,671 A | 1/1997 | Kerwar et al. | |
| 5,681,291 A * | 10/1997 | Galli | A61M 5/2033 |
| | | | 604/156 |
| 6,544,504 B1 | 4/2003 | Grint et al. | |
| 8,664,231 B2 | 3/2014 | Will | |
| 2002/0168360 A1* | 11/2002 | Dingivan | A61P 37/08 |
| | | | 424/143.1 |
| 2005/0153969 A1* | 7/2005 | Warren | A61P 27/02 |
| | | | 514/251 |
| 2014/0179703 A1 | 6/2014 | Will | |
| 2015/0164902 A1 | 6/2015 | Will | |

FOREIGN PATENT DOCUMENTS

WO    WO 2008/009476 A2    1/2008

OTHER PUBLICATIONS

1985 Ed. Physician's Desk Reference ("PDR") (Year: 1985).*
Brooks et al. (1990) Arthritis and Rheumatology 33, 91-94. (Year: 1990).*
American Diabetes Assn. Insulin Administration 26, Diabetes Care Supp. 1 S121-S124 (2003). (Year: 2003).*
Wright et al. International Journal of Pharmaceutics (45) 1988, 237-244 (Year: 1988).*
Ruperto et. "A Randomized Trial of Parenteral Methotrexate Comparing an Intermediate Dose With a Higher Dose in Children With Juvenile Idiopathic Arthritis Who Failed to Respond to Standard Doses of Methotrexate," Arthritis & Rheumatism vol. 50, No. 7, Jul. 2004, pp. 2191-2201 (Year: 2004).*
Alsufyani, K. et al., "The Role of Subcutaneous Administration of Methotrexate in Children With Juvenile Idiopathic Arthritis Who Have Failed Oral Methotrexate" J. Rheumatol 31:179-182 (2003).
Balis F.M. et al., "Pharmacokinetics of Subcutaneous Methotrexate", Journal of Clinical Oncology 6(12):1882-1886 (Dec. 1988).
Black R.L. et al., "Methotrexate Therapy in Psoriatic Arthritis. Double-Blind Study on 21 Patients", J. Am. Med. Assoc 189(10):743-747 (Sep. 1964).
Brooks P.J. et al., "Pharmacokinetics of Methotrexate Administered by Intramuscular and Subcutaneous Injections in Patients With Rheumatoid Arthritis", Arthritis and Rheumatism 33(1):91-94 (Jan. 1990).
Barnhart E.R. (publisher), Physician's Desk Reference for Mexate, 39th Edition, pp. 762-764 (1985).
Feagan B.G. et al., "Methotrexate for the Treatment of Crohn's Disease", The New England Journal of Medicine 332(5):292-297 (Feb. 2, 1995).

(Continued)

*Primary Examiner* — Jeffrey S Lundgren
*Assistant Examiner* — Michael J Schmitt
(74) *Attorney, Agent, or Firm* — Scully, Scott, Murphy & Presser, P.C.

(57) ABSTRACT

Concentrated methotrexate solutions are described which are suitable for the use of an active substance in the production of a parenterally administered medicament for the treatment of inflammatory autoimmune diseases. The methotrexate is added to a pharmaceutically acceptable solvent at a concentration of more than 25 mg/ml.

26 Claims, No Drawings

(56) References Cited

OTHER PUBLICATIONS

Furst D.E. et al., "Increasing Methotrexate Effect With Increasing Dose in the Treatment of Resistant Rheumatoid Arthritis", J. Rheumatol 16(3):313-320 (1989).
Galan N., "How to Select the Correct Needle Size for an Injection", by www.About.com, 4 pages (2015).
Galinsky et al., "Basic Pharmacokinetics and Pharmacodynamics" Remington: The Science and Practice of Pharmacy, pp. 1171 (2006).
Giannini E.H. et al., "Methotrexate in Reistant Juvenile Rheumatoid Arthritis-Results of the USA-USSR Double-Blind, Placebo-Controlled Trial", The New England Journal of Medicine 326(16):1043-1049 (Apr. 16, 1992).
Gubner R., "Therapeutic Suppression of Tissue Reactivity. I. Comparison of the Effects of Cortisone and Aminopterin", Am. J. Med Sci 22:169-175 (1951).
Hoekstra M. et al., "Bioavailability of Higher Dose Methotrexate Comparing Oral and Subcutaneous Administration In Patients With Rheumatoid Arthritis", Journal of Rheumatology 31(4):645-648 (2004).
Hoffmeister R.T., "Methotrexate Therapy in Rheumatoid Arthritis: 15 Years Experience", The American Journal of Medicine 75:69-73 (Dec. 30, 1983).
Hoffmeister R.T., "Methotrexate in Rheumatoid Arthritis", Arthritis and Rheumatism 15(1):S114 (abstract) (Jan.-Feb. 1972).
Jansen M M P M et al., "Methotrexate Outside the Clinic, Intramuscular and Subcutaneous Administration to Patients With Rheumatoid Arthritis", Pharmaceutisch Weekblad 134(46):1592-1596 (1999).
Jorgensen J.T. et al., "Pain Assessment of Subcutaneous Injections", The Annals of Pharmacotherapy 30:729-732 (1996).
Kurnik D. et al., "Bioavailability of Oral vs. Subcutaneous Low-Dose Methotrexate in Patients With Crohn's Disease", Alimentary Pharmacology & Therapeutics 18(1):57-63 (2003).
Michaels R.M. et al., "Weekly Intravenous Methotrexate in the Treatment of Rheumatoid Arthritis", Arthritis and Rheumatism 25(3):339-341 (Mar. 1982).
Muller-Ladner U. et al., "Tolerability and Patient/Physician Satisfaction With Subcutaneously Administered Methotrexate Provided in Two Formulations of Different Drug Concentrations in Patients With Rheumatoid Arthritis", The Open Rheumatology Journal 4:15-22 (2010).
O'Dell J.R., "Methotrexate Use in Rheumatoid Arthritis", Rheumatic Disease Clinics of North America 23(4):779-796 (Nov. 1997).
Pincus T. et al., "Methotrexate as the "Anchor Drug" for the Treatment of Early Rheumatoid Arthritis", Clinical and Experimental Rheumatology 21(Suppl. 31):S179-S185 (2003).
Russo R.A.G. et al., "Tolerance of Parenteral Higher Dose Methotrexate in Children With Juvenile Chronic Arthritis", Clinical and Experimental Rheumatology 18(3):425 (2000).
Silverman E. et al., "Leflunomide or Methotrexate for Juvenile Rheumatoid Arthritis", The New England Journal of Medicine 352:1655-1666 (Apr. 21, 2005).
Weinblatt M.E. et al., "Efficacy of Methotrexate in Rheumatoid Arthritis", British Journal of Rheumatology 34(Suppl. 2):43-48 (1995).
Weinblatt M.E. et al., "Methotrexate in Rheumatoid Arthritis: a Five-Year Prospective Multicenter Study", Arthritis & Rheumatism 37(10):1492-1498 (Oct. 1994).
Weinblatt M.E. et al., "Long Term Prospective Study of Methotrexate the Treatment of Rheumatoid Arthritis: 84-Month Update", Arthritis & Rheumatism 35(2):129-137 (Feb. 1992).
Weinblatt M.E. et al., "Efficacy of Low-Dose Methotrexate in Rheumatoid Arthritis", The New England Journal of Medicine 312:818-822 (Mar. 28, 1985).
Weinblatt M.E., "Methotrexate", Clinical Pharmacology in Rheumatic Diseases, in Textbook of Rheumatology, 4th Edition 1:767-778 (14 pages) (1939).
Wright M.P. et al., "Stability of Methotrexate Injection in Prefilled, Plastic Disposable Syringes", International Journal of Pharmaceutics 45:237-244 (1988).
Zackheim H.S., "Subcutaneous Administration of Methotrexate", Journal of the American Academy of Dermatology 26(6):1008 (1992).
Antares Petition for Inter Partes Review filed by *Antares Pharma, Inc. v. Medac Gesellschaft Fuer Klinische Spezialpraparate MBH* in U.S. Pat. No. 8,664,231 (Jul. 1, 2014).
"Intravenous Therapy", by www.redOrbit.com, 3 pages, (c) (2002-2015).
"Insulin Administration", Diabetes Care, vol. 26, Suppl. 1, pp. S121-S124 (Jan. 2003), 4 pages.
Methotrexate 100 mg/ml Injection Package Insert, Hospira UK Ltd. (Jun. 7, 1994).
Pharmachemie BV, Physician Package Insert, Abitrexate (Feb. 22, 2000).
"Principles of Injection Technique, Guidelines for Needle and Gauge Selection", published by Becton Dixon (BD)© , 1 page (2012).
Product Summary for the "Methotrexate 100 mg/ml Injection" product by Hospira UK Ltd., Date of first authorization Mar. 13, 1987, Date of revision of the text Nov. 22, 2005, 14 pages.
Rote Liste Service, GMBH, Rote Liste 1999ECV, Editio Cantor Verlag, Aulendorf, XP-002491051, Abstract No. 86 042 (1999).
European Search Report dated May 4, 2011 issued in corresponding EP Patent Application No. 10194145.8.
European Opposition Brief dated Sep. 15, 2011 received in correspond EP Patent Application No. 2 046 332 B1.
English-language translation of the Decision issued by the Opposition Division on Nov. 19, 2012 in European Patent No. EP-B-2 046 332.
Ahuja, S. et al., "Handbook of Modern Pharmaceutical Analysis", Academic Press, (2001), vol. 3, 13 pages.
Chereson, R., "Chapter 8: Bioavailability, Bioequivalence, and Drug Selection", Basic Pharmacokinetics, (1996), 7 pages.
"The Cytotoxics Handbook", Fourth Edition, Radcliffe Medical Press LTD, (2002), 4 pages.
"Physicians' Desk Reference", Edward R. Barnhart, (1985), 5 pages.
Volpe, R. et al., "Autoimmune Disease", Encyclopedia of Life Sciences, (2001), pp. 1-7.
Korean Drug Index, 2001, 4 pages, with English-language translation.
Rote Liste (Register for Pharmaceutical Drugs in Germany), 2006, 4 pages, with English-language translation.
Shiroky J.B. et al., "High Dose Intravenous Methotrexate for Refractory Rheumatoid Arthritis", The Journal of Rheumatology, (1992), 19:2, pp. 247-251.
"Consultation on registered medicines, that includes product MIANTREX CS", https://consultas.anvisa.gov.br/#/medicamentos/25351025974200489/?substancia=6706, May 16, 2005, 3 pages.
Unfavorable Opinion dated Sep. 22, 2021 received in BR Patent Application No. PI 0715433-0, 10 pages.

* cited by examiner

CONCENTRATED METHOTREXATE SOLUTIONS

The present invention relates to concentrated methotrexate solutions. In particular, the present invention relates to the use of methotrexate in the production of a parenterally administered medicament for the treatment of inflammatory autoimmune diseases, wherein the methotrexate is present in a pharmaceutically acceptable solvent at a concentration of more than 25 mg/ml. The invention also relates to a ready-made syringe and a carpule containing such a pharmaceutical solution formulation, as well as a pen injector comprising such a carpule and/or a ready-made syringe.

The pharmaceutical active substance N-{4-[(2,4-diamino-6-pteridinylmethyl)methylamino]-benzoyl}-L-glutamic acid (INN: methotrexate, in short: MTX) has been known since the ea 1950s. Methotrexate is a folic acid antagonist. As an antimetabolite of nucleic acid synthesis, it causes an intracellular inhibitation of dehydrofolate reductase (irreversible bond) with a consecutive inhibition of purine synthesis, inhibits $LTB_4$ synthesis in neutrophils, inhibits IL-1 synthesis, suppresses cell-mediated immunity and inhibits endothelial cell proliferation.

Due to its effectiveness as a cytostatic agent, methotrexate has long been used predominantly in the field of oncology. In particular, it was used to treat breast cancer, but also for the treatment of leukemia in children. To this day, methotrexate is still highly significant for the latter indication. The effectiveness of methotrexate in the treatment of psoriasis was discovered early on. Since psoriasis can accompany rheumatoid arthritis, this therapy option was first observed in the late 1950s in individual cases as well.

Rheumatoid arthritis is usually therapeutically treated with fast-acting pain-relieving and short-term anti-inflammatory substances. In this connection, non-steroidal antirheumatics (NSAR, e.g. the active substance diclofenac) and corticoids can be mentioned. However, these substances do not influence the actual course of the disease. In most patients, NSAR and corticoids are only used until the pain and inflammation subside considerably. Then the dosage is often reduced or the drug is tapered completely.

Only disease-modifying anti-rheumatic drugs (DMARDs) have a disease-modifying effect in rheumatoid arthritis. In addition to methotrexate, examples of these substances, which are also referred to as basic therapeutics, include azathioprine, sulfasalazine and anti-malaria substances. Basic therapeutics directly intervene in the course of the disease and can decelerate the progression of the disease, which is why they should be administered as early as possible. Since rheumatoid arthritis is a chronic disease, the basic therapeutics usually have to be taken for long periods of time; if the drugs are effective and well tolerated, the treatment is often continued throughout the patients lifetime (continuous long-term therapy) whereby the dosage of the active substance can be adapted to the course of the disease.

Contrary to chemotherapy in the treatment of tumors, methotrexate as a basic therapeutic in the treatment of rheumatoid arthritis is dosed significantly lower, sometimes up to 1000 times lower, which is why the antirheumatic therapy is also referred to as "low-dosage methotrexate therapy". In Germany, a dosage range of 5.0 to 30.0 mg per week is common for antirheumatic therapy, in other European countries, dosages of up to 40.0 mg per week are administered. It is extremely important that methotrexate only be administered once a week.

In principle, methotrexate can be administered orally and parenterally. However, after a long time of oral therapy based on tablets, parenteral formulations are now being used since it has been found that methotrexate is resorbed more reliably from tablets and thus no sufficient accuracy can be guaranteed in dosage-dependent therapy. Cytostatics suitable for parenteral administration are usually prepared by dissolving the active substance in a suitable solvent, using a specific amount of active substance for each individual patient. However, handling cytostatics and preparing cytostatics-containing medicaments is not without challenges and subject to strict legal restrictions. For example, cytostatics cannot be prepared outside of a suitable venting system provided especially for this purpose. Since rheumatologists and general practitioners usually do not have such systems at their disposal, they are not authorized to prepare methotrexate themselves, whereby even drawing up a syringe from a bottle (for example an injection bottle containing the active substance solution) is considered a preparation.

For this reason, ready-made syringes were developed in order to eliminate this step of drawing up a syringe. For the first time, the applicant in the present invention was able to have such ready-made syringes for subcutaneous application approved throughout Europe. These ready-made syringes allow the use by the physician, the medical staff or, in case of self-application, by the patient himself without a pharmacist having a suitable vent system at his disposal as a go-between.

Ready-made syringes for parenteral administration containing methotrexate solutions wherein the active substance is present at a concentration of up to 25 mg/ml in a pharmaceutically acceptable solvent (trade names: Lantarel® of the company Wyeth, Metex® of the applicant) are known from the prior art for the treatment of rheumatoid arthritis, wherein the injection solution Lantarel® with the concentration 25 mg/ml (trade name: Lantarel® FS 25 mg) is not approved for subcutaneous application. Over the years, methotrexate has become the gold standard in the treatment of rheumatoid arthritis.

As has already been described above, a successful basic therapy with methotrexate requires that the rheumatic patient be administered a suitable dose of methotrexate once a week over a very long period of time, sometimes throughout his entire lifetime. Due to its more advantageous bioavailability, parenteral application is superior to oral application.

Furthermore, children in particular exhibit a certain aversion to taking tablets. However, it has been found that a subcutaneous administration in particular has its difficulties. When treated with the preparations known from the prior art, patients showed a disapproving attitude. This was due to the problem of having to inject the required relatively large amount of active substance solution (e.g. up to 3 ml in the case of a certain dosage) under the skin every week, which was especially difficult to convey to children, including the weekly doctor's visit.

There is therefore a need for pharmaceutical formulations of methotrexate which can be administered to the patient, including children, as easily and pain-free as possible, while providing good bioavailability, over a long period of time at regular intervals, in particular weekly, which therefore leads to a high degree of patient compliance. As an added advantage, the patient should be able to self-administer the pharmaceutical formulation.

The object underlying the present invention is therefore to provide a pharmaceutical formulation for the treatment of inflammatory autoimmune diseases, in particular rheumatoid arthritis, which overcomes the disadvantages of the prior art preparations described above.

The object underlying the present invention is achieved by the subject matter of the patent claims.

In a first embodiment, the invention relates to the use of methotrexate in the production of a parenterally administered medicament for the treatment of inflammatory autoimmune diseases, wherein the methotrexate is present in a pharmaceutically acceptable solvent at a concentration of more than 25 mg/ml.

In another embodiment, the invention relates to a ready-made syringe containing such a pharmaceutical solution formulation of methotrexate in a pharmaceutically acceptable solvent at a concentration of more than 25 mg/ml.

Furthermore, in another embodiment, the invention relates to a carpule containing a pharmaceutical solution formulation of methotrexate in a pharmaceutically acceptable solvent at a concentration of more than 25 mg/ml, as well as a pen injector comprising such a carpule.

According to the present invention, medicaments or pharmaceutical solution formulations are provided which comprise methotrexate at a concentration of more than 25 mg/ml in a pharmaceutically acceptable solvent. In a preferred embodiment, the methotrexate is present in the medicament at a concentration of more than 25 mg/ml to about 150 mg/ml. Furthermore, concentration ranges of 30 mg/ml to 100 mg/ml, and in particular 40 mg/mi to 80 mg/ml and furthermore 50 mg/ml to 75 mg/ml, are preferred. In an especially preferred embodiment, the methotrexate is present in the medicament at a concentration of about 50 mg/ml in a pharmaceutically acceptable solvent.

All solvents which are pharmaceutically acceptable and are not incompatible with the active substance or other possible components of the medicament or the pharmaceutical solution formulation can be used as the pharmaceutically acceptable solvent. According to the present invention, especially suitable solvents include water, in particular water for injection purposes, water comprising isotonization additives and sodium chloride solution, in particular isotonic sodium chloride solution. Water for injection purposes is especially preferred. Examples of isotonization additives include soluble salts (sodium chloride, potassium chloride), sugars (glucose, lactose), sugar alcohols (mannitol, sorbitol) as well as combinations of these additives.

In addition to isotonization additives, the medicament according to the present invention can comprise additives common in the field of pharmaceutical solution formulations. In particular, the medicament according to the present invention can comprise additives with the following functionality: Eu-/isohydration (acetate, phosphate, citrate buffers), antioxidants (ascorbic acid, sulfur compounds common in the technical field), solubility promoters (complexing agents, solubilizers, co-solvents: e.g. cyclodextrine, polyvidone, polysorbate, lecithin, glycocholate), increasing viscosity, adjusting pH (acids, bases, or acidic or basic salts). In an especially preferred embodiment, the pH value of the medicament according to the present invention is between 7.5 and 9.

The medicaments according to the present invention are directed to the treatment of inflammatory autoimmune diseases. The term "inflammatory autoimmune disease" encompasses all inflammatory autoimmune diseases which can reasonably be treated with methotrexate. Examples of inflammatory autoimmune diseases which can be treated with the medicament according to the present invention include, but are not limited to, rheumatoid arthritis, juvenile arthritides, vasculitides, collagenoses, Crohn's disease, colitis ulcerosa, bronchial asthma, Alzheimez's disease, multiple sclerosis, Bechterew's disease, joint arthroses or psoriasis, as well as psoriasis arthritis and in particular plaque-type psoriasis vulgaris. The medicaments of the present invention are especially preferred for the treatment of rheumatoid arthritis, including juvenile arthritides, such as specifically the oligoarthritic and polyarthritic forms of juvenile arthritis.

The medicaments of the present invention are administered parenterally. In particular, the medicaments are administered by intravenous, intramuscular or subcutaneous injection. According to a preferred embodiment of the present invention, the medicament is present in such a form which is suitable for subcutaneous administration. It is furthermore preferred that the medicament be present in a form which allows subcutaneous self-administration by the patient (self-application). Such a treatment of subcutaneous self-administration has for example proven successful in the administration of insulin by the diabetic himself and leads to a high degree of treatment acceptance on the part of the patient (patient compliance). In the case of rhemnatism, self-application also has the advantage that the weekly doctor's visit is no longer necessary.

In a preferred embodiment of the present invention, the medicament according to the present invention is contained in an injection device for a single application, in particular a ready-made syringe. According to the present invention, an injection device for a single application is a device which in addition to a vessel containing the pharmaceutical solution formulation according to the present invention comprises an injection needle (hypodermic needle) through which the medicament can be administered to the patient. Furthermore, such an injection device comprises a mechanical part (e.g. a stamp or a flexible bubble), by means of which the medicament can be pushed from the container through the injection needle. Such an injection device for a single application is furthermore characterized in that it contains a specific single dose of the active substance and thus that during application the vessel containing the pharmaceutical solution formulation according to the present invention has to be emptied completely in order to administer the prescribed dosage. Due to this fact, it is usually unnecessary in this embodiment to add a preservative to the pharmaceutical solution formulation of methotrexate.

An injection device for a single application according to the present invention preferably contains a dose of the active substance methotrexate of 5 mg to 40 mg. It is especially preferred that an injection device for a single application according to the present invention contain a dose of 5.0, 7.5, 10.0, 12.5, 15.0, 17.5, 20.0, 22.5, 25.0, 27.5, 30.0, 32.5, 35.0, 37.5 or 40.0 mg. The volume of the liquid necessary to provide the desired dose, which has to be contained in the injection device for a single application, depends on the concentration of the active substance solution and is obvious to the person skilled in the art. Thus, in order to provide a dose of active substance of 30.0 mg at a methotrexate concentration in the pharmaceutically acceptable solvent of for example 50 mg/ml, an injection device for a single application would have to contain a liquid volume of 0.6 ml.

An especially preferred example of an injection device for a single application according to the present invention is a ready-made syringe. Ready-made syringes are well-known in the pharmaceutical field, in particular also in the treatment of rheumatoid arthritis with methotrexate. Ready-made syringes containing methotrexate solutions with concentrations of 7.5 mg/ml, 10.0 mg/ml and 25 mg/ml are already being distributed on the German market (trade names:

Lantarel® of the company Wyeth, Metex® of the applicant, whereby the commercial product Lantarel® FS 25 mg is not approved for subcutaneous application). Although the provision of methotrexate solutions in ready-made syringes, some for self-application, have had a positive impact on patient compliance, the prior art preparations that are approved for subcutaneous application have the disadvantage that, depending on the amount of active substance to be administered in each week, relatively large amounts of liquid have to be injected under the patient's skin. In the case of a common weekly dosage of active substance of 30 mg, this means that based on the currently highest concentration of active substance solution for subcutaneous application of the prior art, namely 10 mg/ml (in the commercial product Metex® 10 mg/ml of the applicant), a volume of 3 ml has to be injected under the skin. This large amount of liquid is often hard to convey to the patient, in particular children, which leads to a reduced patient compliance.

The medicaments provided by the present invention on the other hand contain highly concentrated solutions of the active substance methotrexate which results in a reduction of the amount of liquid to be administered with a certain weekly active substance dosage. For example, in the case of an especially preferred concentration of 50 mg/ml according to the present invention, it would be sufficient to administer a liquid volume of only 0.6 ml subcutaneously in order to keep with a weekly active substance dosage of 30 mg. It can be expected that this has a positive impact on patient compliance.

Thus, in a preferred embodiment, the present invention provides a ready-made syringe containing a pharmaceutical solution formulation of methotrexate at a concentration of more than 25 mg/ml in a pharmaceutically acceptable solvent. Ready-made syringes are well known in the pharmaceutical field and are not restricted in any way in the present invention. Ready-made syringes according to the present invention for example also encompass disposable injection systems such as the Uniject® injection system. In one embodiment, the ready-made syringe can already be provided with a suitable hypodermic needle for intravenous, intramuscular or subcutaneous injection; in an alternative embodiment, the ready-made syringe is at first provided with a rubber tip or the like which prior to application is replaced with a separately packaged sterile hypodermic needle by the physician, the medical staff, or, in case of self-application, by the patient himself.

Preferably, the ready-made syringe according to the present invention is designed such that it is suitable for the subcutaneous application of the active substance solution, which can be achieved by providing a hypodermic needle suitable for subcutaneous injection. In a preferred embodiment, the ready-made syringe is constructed such that even rheumatic patients with limited fine motor skills who may not necessarily be able to self-inject a medicament with conventional ready-made syringes, can carry out a self-administration. In particular, the stamp and back stop are constructed and sized such that handling is facilitated for the rheumatic patient. Ready-made syringes with that type of design are known in the prior art.

In another preferred embodiment of the present invention, the medicament according to the present invention is contained in a storage container. A storage container according to the present invention can be any container commonly used in the technical field in which the medicament or the pharmaceutical solution formulation according to the present invention can be filled and stored professionally, i.e. in particular in a sterile manner. Examples of storage containers include, but are not limited to, an injection bottle, a vial, a bag, a glass ampoule, or a carpule. According to an embodiment of the present invention, in order to administer the medicament to the patient, the desired amount of pharmaceutical solution formulation first has to be drawn up from the storage container (for example an injection bottle) by means of an injection device (for example a conventional disposable syringe), while according to an alternative embodiment of the present invention the pharmaceutical solution formulation can be administered directly from the storage container (for example a carpule) by means of an injection device (for example a pen injector).

In a preferred embodiment of the invention the storage container comprises, in addition to the active substance methotrexate dissolved in the pharmaceutically acceptable solvent, at least one preservative. The preservative suitable for use in the present invention is not particularly restricted and a person skilled in the art will have no difficulties selecting a suitable preservative from the preservatives commonly used for pharmaceutical purposes. Preferred preservatives include cresols, benzyl alcohols, and phenyl ethyl alcohols. The main purpose of the preservative is to preserve the pharmaceutical solution formulation remaining in the storage container according to the present invention (for example an injection bottle or a carpule) after a portion of the medicament has been removed (for example by means of a conventional disposable syringe or a pen injector).

The total dosage amount of the active substance methotrexate in a storage container according to the present invention is not particularly restricted and in addition to the used concentration of methotrexate in the pharmaceutically acceptable solvent is largely determined by the dimensions of the storage container and thus the amount of liquid the storage container can accommodate. Preferably, the storage container of the present invention contains a total dosage amount of 5 to 5,000 mg methotrexate.

A preferred example of a storage container containing the medicament according to the present invention is a carpule. Carpules, also referred to as syringe cartridges, are well known in the art. To the person skilled in the art, a carpule is a preferably cylindrical sterile drug receptacle preferably made from glass or a preferably transparent inert plastic (e.g. Topas®). On one side of carpule cylinder there is usually a movable end plug, and on the other side a pierceable membrane made from rubber or a comparable elastic scaling material. For the application of the medicament, the pharmaceutical preparation in the carpule is pressed out of the carpule through a hypodermic needle which pierces the rubber membrane described above by exerting pressure on the movable end plug with e.g. an external stamp or piston.

In another embodiment, the present invention therefore provides a carpule containing a pharmaceutical solution formulation of methotrexate at a concentration of more than 25 mg/ml in a pharmaceutically acceptable solvent. In a preferred embodiment, the carpule according to the present invention contains a total dosage amount of 5 to 500 mg, especially preferred 7.5 to 300 mg, of methotrexate.

The medicament is preferably administered from the carpule by means of an injection device. In an especially preferred embodiment of the present invention, the carpule is therefore suitable for the application of the medicament via an injection device. Such injection devices are well known in the art. Preferably, one such injection device is a so-called pen injector, into which the carpule can be inserted. Pen injectors usually look like large fountain pens and are in particular commonly used by diabetics for comfortably injecting the insulin dose they require. After the inserted carpule has been emptied, a new carpule can easily be inserted in the pen injector (comparable to the replacement of an ink cartridge in the fountain pen mentioned above as a comparison).

Thus, in another embodiment, the present invention provides a pen injector comprising the above-described carpule of the present invention containing the medicament of the present invention.

A pen injector according to the present invention is preferably designed such that it is suitable for the subcutaneous application of the active substance which can in particular be achieved by the provision of a hypodermic needle suitable for subcutaneous injection. Furthermore, a pen injector according to the present invention and the carpule contained therein are preferably designed such that multiple applications of single dosages can be carried out. For this purpose, a pen injector according to the present invention preferably comprises a structural device (e.g. a control dial) by means of which a certain dosage of the methotrexate to be administered can be adjusted (i.e. specifically the selection of a certain application volume in combination with a known active substance concentration of methotrexate in the pharmaceutical solution formulation) by the physician, the medical staff, or, in case of self-application, by the patient himself. Thus, with this embodiment, the present invention also offers the possibility of selecting, if desired, intermediate dosages for which no other storage containers or injection devices, in particular no other injection bottles or ready-made syringes, are commercially available. Pen injectors with that type of structure are well known in the art, especially from the field of insulin injectors.

According to a preferred embodiment of the invention, a pen injector according to the present invention is designed such that the single dosages per application can be adjusted from 5 to 40 mg methotrexate. In particular, a pen injector according to the present invention can be adjusted such that per application a single dosage of 5.0, 7.5, 10.0, 12.5, 15.0, 17.5, 20.0, 22.5, 25.0, 27.5, 30.0, 32.5, 35.0, 37.5 or 40.0 mg can be administered.

The invention is described in more detail in the following examples which are not intended to restrict the invention in any way:

EXAMPLES

Example 1

The methotrexate solution described below (concentration: 50 mg/ml) was prepared from the following components.

| | |
|---|---|
| Methotrexate: | 1,500 g |
| Sodium chloride: | 120 g |
| Sodium hydroxide: | 300 g |
| Water for injection purposes: | 28,764 g |
| Total: | 30,684 g = 30 liters |

For preparing the solution (Example 1), about 60% of the required water for injection purposes (20-25° C.) was provided in the solution vessel. The agitator was switched on and the amount of sodium chloride listed above was added and dissolved completely. The vessel and the solution were flooded with nitrogen, which essentially displaced the residual dissolved oxygen. The amount of methotrexate listed above was suspended in the solution while the agitator was running. The pH value of the solution was adjusted to a value between 8.5 and 8.9 using 1% sodium hydroxide solution (prepared from NaOH and water for injection purposes). The temperature of the solution is between 20 and 30° C. A clear solution is obtained whose pH is stable between 8.5 and 8.9. The final volume was obtained by adding the remaining amount of water for injection purposes.

By means of sterile filtration through a 0.22 µm sterile filter the solution was filled into the provided sterile glass receptacles of glass type 1 (carpules or ready-made syringes) using protective gas (nitrogen) under clean-room conditions (class A).

Example 2

The methotrexate solution described below (concentration: 50 mg/ml) was prepared from the following components.

| | |
|---|---|
| Methotrexate disodium: | 1,645 g |
| Sodium chloride: | 120 g |
| Water for injection purposes: | ad 30,684 g |
| Total: | 30,684 g = 30 liters |

For preparing the solution (Example 2), about 60% of the required water for injection purposes (20-25° C.) was provided in the solution vessel. The agitator was switched on and the amount of sodium chloride listed above was added and dissolved completely. The vessel and the solution were flooded with nitrogen, which essentially displaced the residual dissolved oxygen. The amount of methotrexate listed above was dissolved in the solution while the agitator was running. The temperature of the solution is between 20 and 30° C. The solution is clear and the pH value is stable between 8.5 and 8.9. The final volume was obtained by adding the remaining amount of water for injection purposes.

By means of sterile filtration through a 0.22 µm sterile filter the solution was filled into the provided sterile glass receptacles of glass type 1 (carpules or ready-made syringes) using protective gas (nitrogen) under clean-room conditions (class A).

What is claimed is:

1. A method for treating juvenile arthritis in a juvenile patient in need thereof, the method comprising subcutaneously administering to said juvenile patient a pharmaceutical solution comprising methotrexate dissolved in a pharmaceutically acceptable solvent at a concentration of 40 to 150 mg/ml, wherein the pharmaceutical solution is contained in a ready-made single-application syringe when administered to the patient.

2. The method according to claim 1, wherein said methotrexate is present at a concentration of 50 to 150 mg/ml.

3. The method according to claim 1, wherein said methotrexate is present at a concentration of 50 to 100 mg/ml.

4. The method according to claim 1, wherein said methotrexate is present at a concentration of 50 to 75 mg/ml.

5. The method according to claim 1, wherein the pharmaceutically acceptable solvent is selected from water, water for injection purposes, water comprising isotonization additives, and sodium chloride solution.

6. The method according to claim 1, wherein the pharmaceutically acceptable solvent is isotonic sodium chloride solution.

7. The method according to claim 1, wherein the pharmaceutical solution further comprises a preservative.

8. The method according to claim 1, wherein the syringe is a pen injector.

9. The method according to claim 1, wherein the syringe contains a dosage of 5 to 40 mg of methotrexate and said dosage is administered to the patient.

10. The method according to claim 1, wherein the syringe contains a dosage of 5.0, 7.5, 10.0, 12.5, 15.0, 17.5, 20.0, 22.5, 25.0, 27.5, 30.0, 32.5, 35.0, 37.5 or 40.0 mg of methotrexate and said dosage is administered to the patient.

11. The method according to claim 1, wherein the syringe contains a dosage of 5 to 22.5 mg of methotrexate and said dosage is administered to the patient.

12. The method according to claim 1, wherein the syringe contains a dosage of 5.0, 7.5, 10.0, 12.5, 15.0, 17.5, 20.0, or 22.5 mg of methotrexate and said dosage is administered to the patient.

13. The method according to claim 1, wherein the pharmaceutical solution is contained in a storage container.

14. The method according to claim 13, wherein the storage container contains a total dosage amount of 5 to 5,000 mg.

15. The method according to claim 13, wherein the storage container is an injection bottle, a vial, a bag, a glass ampoule, or a carpule.

16. The method according to claim 13, wherein the storage container is a carpule.

17. The method according to claim 13, wherein the syringe is a pen injector.

18. The method according to claim 16, wherein said carpule contains a total dosage amount of 5 to 5,000 mg.

19. The method according to claim 16, wherein the carpule and the syringe are effective to provide administration of multiple applications of single dosages.

20. The method according to claim 19, wherein the single dosages per application are adjusted to 5 to 40 mg of methotrexate.

21. The method according to claim 20, wherein the single dosages of methotrexate per application are adjusted to 5.0, 7.5, 10.0, 12.5, 15.0, 17.5, 20.0, 22.5, 25.0, 27.5, 30.0, 32.5, 35.0, 37.5 or 40.0 mg of methotrexate.

22. The method according to claim 19, wherein the single dosages per application are adjusted to 5 to 22.5 mg of methotrexate.

23. The method according to claim 19, wherein the single dosages per application are adjusted to 5.0, 7.5, 10.0, 12.5, 15.0, 17.5, 20.0, or 22.5 mg of methotrexate.

24. The method according to claim 1, wherein the juvenile arthritides is an oligoarthritic form of juvenile arthritides.

25. The method according to claim 1, wherein the juvenile arthritides is a polyarthritic form of juvenile arthritides.

26. The method according to claim 1, wherein a volume of no more than 0.6 mL is subcutaneously administered.

* * * * *